US011426287B2

(12) United States Patent
McLaughlin et al.

(10) Patent No.: US 11,426,287 B2
(45) Date of Patent: Aug. 30, 2022

(54) EXPANDABLE VERTEBRAL IMPLANT

(71) Applicant: GLOBUS MEDICAL, INC., Audubon, PA (US)

(72) Inventors: Colm McLaughlin, Glenside, PA (US); Jason Gray, East Greenville, PA (US); James Himmelberger, Souderton, PA (US)

(73) Assignee: Globus Medical Inc., Audubon, PA (US)

( * ) Notice: Subject to any disclaimer, the term of this patent is extended or adjusted under 35 U.S.C. 154(b) by 173 days.

(21) Appl. No.: 16/454,391

(22) Filed: Jun. 27, 2019

(65) Prior Publication Data

US 2019/0314162 A1    Oct. 17, 2019

Related U.S. Application Data

(63) Continuation of application No. 15/274,570, filed on Sep. 23, 2016, now Pat. No. 10,369,000, which is a
(Continued)

(51) Int. Cl.
*A61F 2/44* (2006.01)
*A61F 2/46* (2006.01)
(Continued)

(52) U.S. Cl.
CPC .............. *A61F 2/4455* (2013.01); *A61F 2/44* (2013.01); *A61F 2/4465* (2013.01); *A61F 2/4611* (2013.01); *A61F 2002/2817* (2013.01); *A61F 2002/2835* (2013.01); *A61F 2002/3055* (2013.01); *A61F 2002/30383* (2013.01); *A61F 2002/30393* (2013.01); *A61F 2002/30395* (2013.01); *A61F 2002/30405* (2013.01); *A61F 2002/30495* (2013.01);
(Continued)

(58) Field of Classification Search
CPC ....... A61F 2/4455; A61F 2/4465; A61F 2/447
See application file for complete search history.

(56) References Cited

U.S. PATENT DOCUMENTS 3,741,251 A    6/1973 Rees
4,126,338 A    11/1978 Coel et al.
(Continued)

FOREIGN PATENT DOCUMENTS

DE    4012622 C1    7/1991
DE    4327054 C1    4/1995
(Continued)

*Primary Examiner* — Julianna N Harvey

(57) ABSTRACT

Expandable implants for engagement between vertebrae generally include an inner member, outer member, and gear member positioned coaxial with respect to each other such that the inner and outer members are moveable relative to each other along an axis. The gear member is axially fixed to the outer member and freely rotatable with respect to the outer member and the gear member threadedly engages a threaded portion of the inner member to translate inner member along the axis. The implant is configured to engage the vertebrae in a predetermined alignment and the gear member includes gear teeth exposed to the exterior and configured to be accessible by a tool member at a plurality of angular positions around the perimeter of the implant device.

19 Claims, 11 Drawing Sheets

Related U.S. Application Data continuation of application No. 14/819,778, filed on Aug. 6, 2015, now Pat. No. 9,474,621, which is a continuation of application No. 13/048,604, filed on Mar. 15, 2011, now Pat. No. 9,579,211, which is a continuation-in-part of application No. 12/758,529, filed on Apr. 12, 2010, now Pat. No. 8,282,683.

(51) Int. Cl.
  *A61F 2/30* (2006.01)
  *A61F 2/28* (2006.01)

(52) U.S. Cl.
  CPC ............ *A61F 2002/30523* (2013.01); *A61F 2002/30576* (2013.01); *A61F 2002/30578* (2013.01); *A61F 2002/30579* (2013.01); *A61F 2002/30593* (2013.01); *A61F 2002/30594* (2013.01); *A61F 2002/30601* (2013.01); *A61F 2002/30858* (2013.01); *A61F 2002/4625* (2013.01); *A61F 2002/4627* (2013.01); *A61F 2002/4629* (2013.01); *A61F 2310/00011* (2013.01); *A61F 2310/00023* (2013.01); *A61F 2310/00131* (2013.01)

(56) References Cited

U.S. PATENT DOCUMENTS

| | | |
|---|---|---|
| 4,341,482 A | 7/1982 | Wollensak |
| 4,401,112 A | 8/1983 | Rezalan |
| 4,599,086 A | 7/1986 | Doty |
| 4,657,550 A | 4/1987 | Daher |
| 4,792,320 A | 12/1988 | Nickel |
| 5,123,926 A | 6/1992 | Pisharodi |
| 5,234,378 A | 8/1993 | Helgesen et al. |
| 5,290,312 A | 3/1994 | Kojimoto et al. |
| 5,306,310 A | 4/1994 | Siebels |
| 5,375,823 A | 12/1994 | Navas |
| 5,496,216 A | 3/1996 | Rohrle et al. |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,601,493 A | 2/1997 | Nakazono et al. |
| 5,653,763 A | 8/1997 | Errico et al. |
| 5,665,122 A | 9/1997 | Kambin |
| 5,676,701 A | 10/1997 | Yuan et al. |
| 6,010,290 A | 1/2000 | Slesinski |
| 6,344,057 B1 | 2/2002 | Rabbe |
| 6,524,341 B2 | 2/2003 | Lang |
| 6,723,126 B1 | 4/2004 | Berry |
| 6,730,088 B2 * | 5/2004 | Yeh .......................... A61F 2/44 606/247 |
| 6,835,159 B2 | 12/2004 | Gehring et al. |
| 6,866,682 B1 * | 3/2005 | An ........................... A61F 2/44 623/17.15 |
| 6,902,579 B2 | 6/2005 | Harms |
| 6,953,477 B2 | 10/2005 | Berry |
| 6,972,019 B2 | 12/2005 | Michelson |
| 6,976,816 B2 | 12/2005 | Slesinski et al. |
| 7,056,343 B2 | 6/2006 | Schafer et al. |
| 7,077,864 B2 | 7/2006 | Byrd, III |
| 7,135,043 B2 | 11/2006 | Nakahara |
| 7,204,853 B2 | 4/2007 | Gordon et al. |
| 7,316,714 B2 | 1/2008 | Gordon et al. |
| 7,442,209 B2 | 10/2008 | Michelson |
| 7,544,208 B1 | 6/2009 | Mueller et al. |
| 7,588,573 B2 | 9/2009 | Berry |
| 7,641,693 B2 | 1/2010 | Gütlin et al. |
| 7,674,296 B2 | 3/2010 | Rhoda |
| 7,691,147 B2 | 4/2010 | Gütlin et al. |
| 7,708,779 B2 | 5/2010 | Edie |
| 7,758,648 B2 | 7/2010 | Castleman |
| 7,776,091 B2 | 8/2010 | Mastrorio |
| 7,794,502 B2 | 9/2010 | Michelson |
| 7,811,327 B2 | 10/2010 | Hansell |
| 7,846,207 B2 | 12/2010 | Lechmann |
| 7,862,616 B2 | 1/2011 | Lechmann |
| 7,879,096 B2 | 2/2011 | Dickson |
| 7,909,869 B2 | 3/2011 | Gordon et al. |
| 7,909,870 B2 | 3/2011 | Kraus |
| 7,914,581 B2 | 3/2011 | Dickson |
| 7,972,363 B2 | 7/2011 | Moskowitz |
| 7,985,255 B2 | 7/2011 | Bray |
| 8,034,111 B2 | 10/2011 | Hsu |
| 8,123,810 B2 | 2/2012 | Gordon et al. |
| 8,161,619 B2 | 4/2012 | Wanthal |
| 8,430,759 B2 | 4/2013 | Wanthal |
| 8,647,386 B2 | 2/2014 | Gordon et al. |
| 8,721,723 B2 | 5/2014 | Hansell et al. |
| 2004/0172129 A1 | 9/2004 | Schafer et al. |
| 2004/0193272 A1 | 9/2004 | Zubok et al. |
| 2005/0281613 A1 | 12/2005 | Tella et al. |
| 2006/0058877 A1 | 3/2006 | Gutlin |
| 2006/0085071 A1 | 4/2006 | Lechmann et al. |
| 2006/0100710 A1 * | 5/2006 | Gutlin ........................ A61F 2/44 623/17.15 |
| 2006/0241762 A1 | 10/2006 | Kraus |
| 2006/0241770 A1 * | 10/2006 | Rhoda ...................... A61F 2/442 623/17.15 |
| 2006/0293755 A1 | 12/2006 | Lindner |
| 2007/0028710 A1 * | 2/2007 | Kraus ..................... A61F 2/4611 74/400 |
| 2007/0191954 A1 | 8/2007 | Hansell |
| 2007/0250171 A1 | 10/2007 | Bonin, Jr. |
| 2007/0255407 A1 | 11/2007 | Castleman |
| 2007/0255409 A1 * | 11/2007 | Dickson .............. A61F 2/30744 623/17.11 |
| 2007/0255410 A1 | 11/2007 | Dickson et al. |
| 2007/0255415 A1 | 11/2007 | Edie |
| 2008/0015704 A1 | 1/2008 | Gradl et al. |
| 2008/0183293 A1 | 7/2008 | Parry |
| 2008/0243254 A1 * | 10/2008 | Butler ....................... A61F 2/44 623/17.16 |
| 2008/0281424 A1 | 11/2008 | Parry |
| 2009/0043393 A1 | 2/2009 | Duggal et al. |
| 2009/0088853 A1 | 4/2009 | Ogilvie et al. |
| 2009/0112320 A1 | 4/2009 | Kraus |
| 2009/0112324 A1 | 4/2009 | Refai |
| 2009/0112325 A1 | 4/2009 | Refai |
| 2009/0138089 A1 | 5/2009 | Doubler |
| 2009/0164017 A1 | 6/2009 | Sommerich |
| 2009/0164019 A1 * | 6/2009 | Hsu .......................... A61F 2/44 623/17.16 |
| 2009/0182430 A1 | 7/2009 | Tyber |
| 2009/0192613 A1 | 7/2009 | Wing |
| 2009/0210061 A1 | 8/2009 | Sledge |
| 2009/0234455 A1 | 9/2009 | Moskowitz |
| 2010/0070029 A1 | 3/2010 | Drews et al. |
| 2010/0094424 A1 * | 4/2010 | Woodburn ................ A61F 2/44 623/17.16 |
| 2010/0106251 A1 | 4/2010 | Kast |
| 2010/0145460 A1 | 6/2010 | Mcdonough |
| 2010/0179655 A1 | 7/2010 | Hansell |
| 2010/0185297 A1 | 7/2010 | Steinberg |
| 2010/0274357 A1 | 10/2010 | Miller |
| 2010/0280614 A1 | 11/2010 | Castleman |
| 2010/0286787 A1 | 11/2010 | Villiers |
| 2010/0298942 A1 | 11/2010 | Hansell |
| 2011/0087328 A1 | 4/2011 | Dickson |
| 2011/0097174 A1 | 4/2011 | Varden |
| 2011/0178598 A1 | 7/2011 | Rhoda |
| 2011/0184424 A1 | 7/2011 | Isch et al. |
| 2011/0184524 A1 | 7/2011 | Wiedenbeck |
| 2011/0196493 A1 | 8/2011 | Pimenta |
| 2011/0218631 A1 | 9/2011 | Woodburn et al. |
| 2011/0251691 A1 | 10/2011 | McLaughlin |
| 2011/0251692 A1 | 10/2011 | McLaughlin |
| 2012/0130493 A1 | 5/2012 | McLaughlin et al. |

(56) References Cited

U.S. PATENT DOCUMENTS

| | | | | |
|---|---|---|---|---|
| 2012/0209384 A1* | 8/2012 | Arnold | ............... | A61F 2/4465 |
| | | | | 623/17.15 |
| 2012/0265303 A1 | 10/2012 | Refai et al. | | |
| 2014/0156006 A1* | 6/2014 | Bannigan | ............ | A61F 2/4455 |
| | | | | 623/17.15 |

FOREIGN PATENT DOCUMENTS

| | | |
|---|---|---|
| EP | 0576379 B1 | 6/1993 |
| EP | 0610837 B1 | 7/1994 |
| SU | 1424826 A1 | 9/1988 |
| WO | 9201428 A1 | 2/1992 |
| WO | 9525485 A1 | 9/1995 |
| WO | 2010027359 A1 | 3/2010 |

\* cited by examiner

EXPANDABLE VERTEBRAL IMPLANT

CROSS-REFERENCE TO RELATED APPLICATIONS

This application is a continuation of U.S. patent application Ser. No. 15/274,570, filed Sep. 23, 2016 (published as U.S. Pat. Pub. No. 2017-0007423), which is a continuation of U.S. patent application Ser. No. 14/819,778, filed Aug. 6, 2015 (now U.S. Pat. No. 9,474,621), which is a continuation of U.S. patent application Ser. No. 13/048,604, filed Mar. 15, 2011 (now U.S. Pat. No. 9,579,211), which is a continuation-in-part of U.S. patent application Ser. No. 12/758,529, filed on Apr. 12, 2010 (now U.S. Pat. No. 8,282,683), the entire contents of which are hereby incorporated by reference in their entireties for all purposes.

FIELD OF THE INVENTION

The present invention relates to a device to support the spine after removal of at least a part of a vertebra.

BACKGROUND OF THE INVENTION

When a vertebra is damaged or diseased, surgery may be used to replace the vertebra or a portion thereof with a prosthetic device to restore spinal column support. For example, vertebral body replacement is commonly required in the treatment of vertebral fracture, tumor, or infection.

In recent years, several artificial materials and implants have been developed to replace the vertebral body, such as, for example, titanium cages, ceramic, ceramic/glass, plastic or PEEK, and carbon fiber spacers. Recently, various expandable prosthetics or expandable cages have been developed and used for vertebral body replacement. The expandable prosthetic devices are generally adjustable to the size of the cavity created by a corpectomy procedure and typically are at least partially hollow to accommodate bone cement or bone fragments to facilitate fusion in vivo. Some expandable implants may be adjusted prior to insertion into the cavity, while others may be adjusted in situ. Two advantages of the vertebral body replacement using an expandable prosthetic device that is adjustable in situ is that it is easy to place or insert and it permits an optimal, tight fit and correction of the deformity by in vivo expansion of the device. Some other advantages offered by an expandable prosthetic device are that they can facilitate distraction across the resected vertebral defect for correction of the deformity, and allow immediate load bearing after corpectomy.

Instrumentation and specialized tools for insertion of a vertebral implant is one important design parameter to consider when designing a vertebral implant. Spinal surgery procedures can present several challenges because of the small clearances around the prosthetic when it is being inserted into position. Another important design consideration includes the ability of the device to accommodate various surgical approaches for insertion of the vertebral implant.

SUMMARY OF THE INVENTION

The present invention relates to an expandable prosthetic implant device for engagement between vertebrae generally comprising an inner member, outer member, and gear member positioned coaxial with respect to each other such that the inner and outer members are moveable relative to each other along an axis. The inner member has a hollow interior portion and a threaded external portion and includes a first end portion configured to engage an endplate which is capable of engaging a first vertebral body. The outer member has a hollow interior portion configured to receive the inner member and includes a second end portion configured to engage an endplate which is capable of engaging a second vertebral body. The gear member is axially fixed to the outer member and freely rotatable with respect to the outer member and the gear member threadedly engages the threaded portion of the inner member.

The implant is configured to engage the vertebrae such that first and second end portions are oriented in a predetermined alignment with respect to the first and second vertebral bodies. The gear member includes teeth extending around the perimeter of the gear member and the teeth are exposed to the exterior and configured to be accessible by a tool member.

BRIEF DESCRIPTION OF THE DRAWINGS

The present invention will be more readily understood with reference to the embodiments thereof illustrated in the attached drawing figures, in which.

Throughout the drawing figures, it should be understood that like numerals refer to like features and structures.

DETAILED DESCRIPTION OF THE PREFERRED EMBODIMENTS

Figure 1:
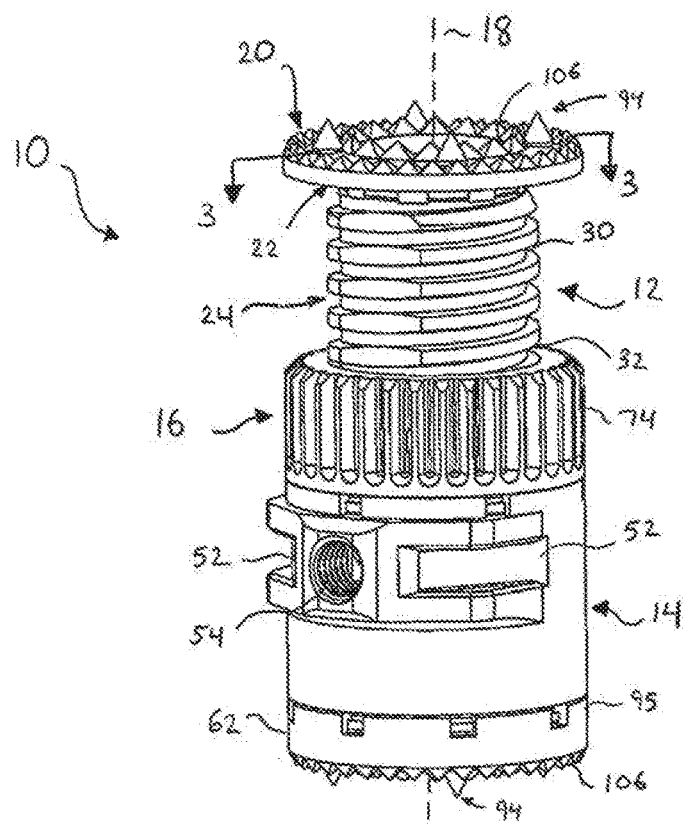
FIG. 1 is a perspective view of an implant in accordance with an embodiment of the present invention.

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Referring to FIGS. 1-6, a preferred embodiment of an expandable vertebral implant 10 is shown. The implant 10 preferably comprises an inner member 12 which may be telescopingly received within an outer member 14. The implant 10 further comprises a gear member 16 generally configured to effect translation of the inner member 12 with respect to the outer member 14 thereby allowing for expansion and contraction of the implant 10. The inner member 12, the outer member 14, and the gear member 16 are preferably centered along a longitudinal axis 18 and define a hollow interior portion which may be filled with bone material, bone growth factors, bone morphogenic proteins, or other materials for encouraging bone growth, blood vessel growth or growth of other tissue through the many apertures in the device. In one preferred embodiment, members 12, 14, and 16 are made of a polyether ether ketone (PEEK) plastic material. There are several known advantages of PEEK plastic material including being radiolucent, having a mechanical strength that is close to bone, and may be more easily sterilized than other plastics. In alternate preferred embodiments, the members 12, 14, and 16 may be made of a biologically inert metal alloys, such as titanium, or other suitable materials.

Referring to FIGS. 1-5, the inner member 12 has a generally cylindrical body 24 with a distal end 22 and a proximal end 36. In a preferred embodiment, the body 24 of the inner member 12 comprises an inner surface 28 and an outer surface 30 and generally defines a hollow interior portion 23 extending axially therethrough. At least part of the outer surface 30 preferably includes external threads 32. Located proximate to the distal end 22 of the body 24 are a plurality of tabs 38 which assist in connecting and positionally locating an endplate 20. In a preferred embodiment, the body 24 is configured and dimensioned to be cooperatively received within outer member 14.

Figure 5:
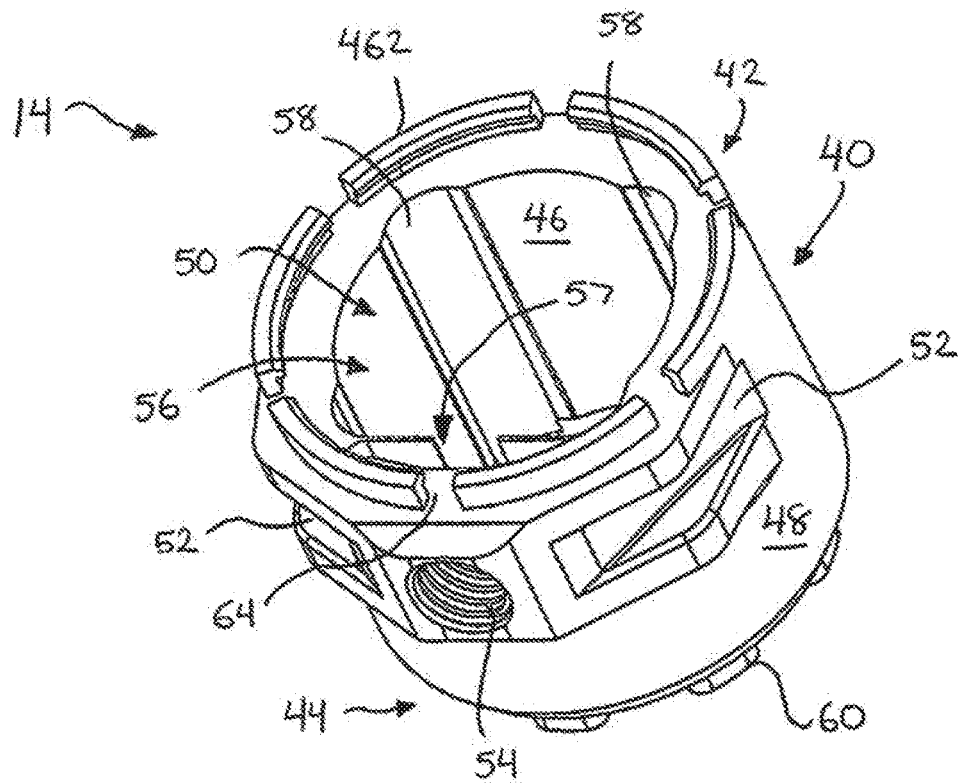
FIG. 5 is perspective view of an embodiment of an outer member of the implant of FIG. 1.

The outer member 14 has a generally cylindrical body 40 with a distal end 42 and a proximal end 44. In a preferred embodiment, the body 40 of the outer member 14 comprises an inner surface 46 and an outer surface 48 and generally defines a hollow interior portion 50 extending axially therethrough. The outer surface 48 preferably has at least one slot 52 and an opening 54 configured and dimensioned to receive a portion of an implantation tool. In a preferred embodiment, the opening 54 extends from the outer surface 48 to the hollow interior portion 50 and at least a portion of the opening 54 is threaded. As best seen in FIG. 5, the inner surface 46 includes a channel 57 for receiving a locking member (discussed below). Located proximate to the proximal end 44 of the outer member 14 are a plurality of tabs 60 which assist in connecting and positionally locating an endplate 62. In a preferred embodiment, a lip 462 is formed around the exterior of the distal end 42 of body 40 and is configured to cooperatively fit with a portion of the gear member 16. A plurality of relief spaces or slots 64 are radially spaced around lip 462 to facilitate a snapping engagement of the lip 462 with the gear member 16. In this regard, slots 64 allow the lip 462 to deform slightly and contract in the radial direction to accommodate gear member 16 to snap on to lip 462. In a preferred embodiment, the interior portion 50 of body 44 is configured and dimensioned to cooperatively receive body 24 of inner member 12 within outer member 14. In this regard, the dimensions of interior portion 50 of body 44 are greater than dimensions of body 24 of inner member 12.

As best seen in FIGS. 2-5, in a preferred embodiment of a prosthetic device 10, the body 24 of the inner member 12 includes a flattened portion 34 which extends at least in part from the distal end 22 to the proximal end 36 and includes a base member 37 having at least one lobe 39 located proximate to the distal end 36 of the body 24. Focusing on FIG. 5, the body 40 of the outer member 14 includes a flattened area 56 and at least one depression 58 on the inner surface 46. When the inner member 12 is assembled within the outer member 14, the flattened area 56 of the outer member 14 cooperatively aligns with the flattened portion 34 of the inner member 12 and the at least one depression 58 of outer member 14 receives the at least one lobe 39 of the inner member 12. The flattened portion 34 and the flattened area 56 along with the lobes 39 and the depressions 58 cooperate to allow the inner member 12 to linearly move with respect to the outer member 14 but prevent the inner member 12 from rotating with respect to the outer member 14. In addition, the base member 37 serves as a stop preventing the inner member 12 from rotating to a point of disengagement from outer member 14.

Figure 6:
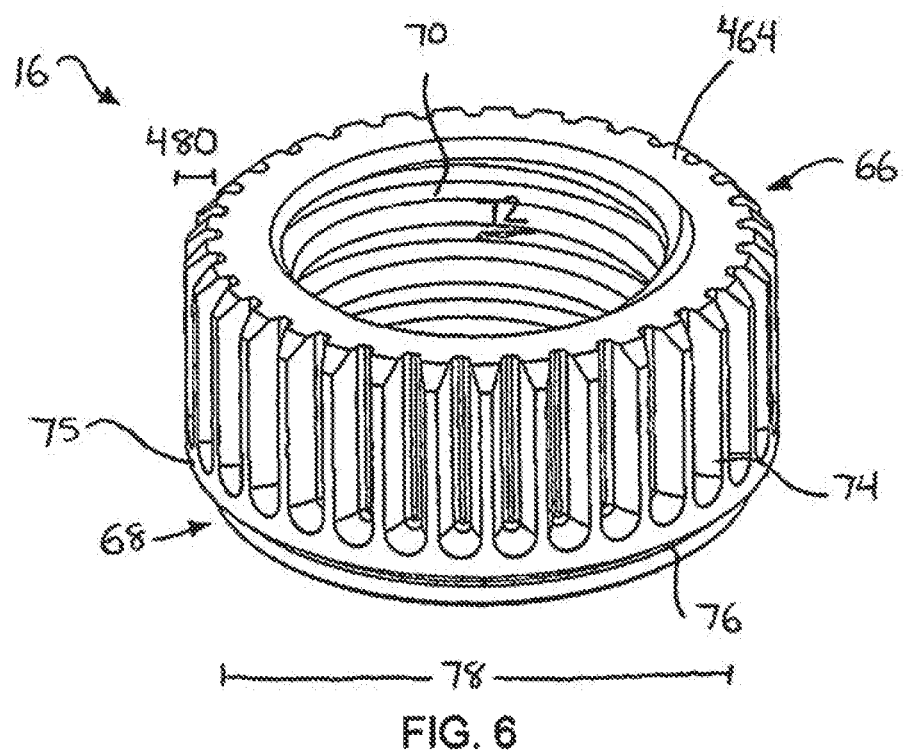
FIG. 6 is an elevated perspective view of one embodiment of a gear member of the implant of FIG. 1.
Figure 7:
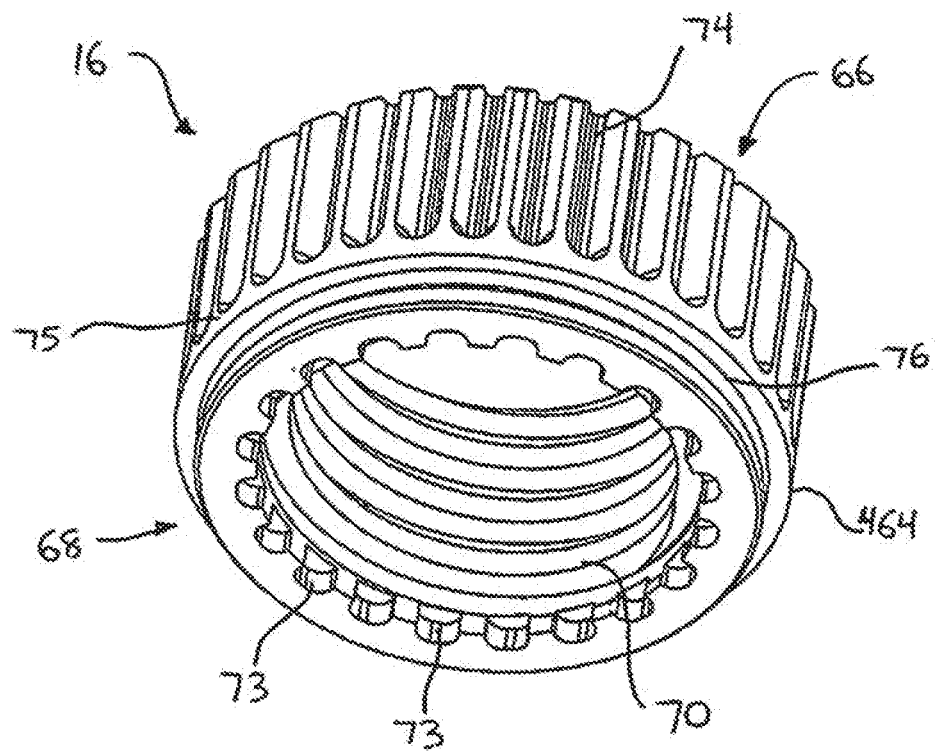
FIG. 7 is a bottom perspective view of the gear member of FIG. 6.

Referring now to FIGS. 6-7, a gear member 16 comprises a generally hollow body 464 extending from a distal end 66 to a proximal end 68 with a helical thread 70 along at least part of an inner wall 72 and an array of gear teeth 74 along a portion of the exterior wall 75. The gear member 16 is generally configured to rotatably connect to the distal end 42 of the outer member 14 and the internal helical thread 70 is configured to engage the external threads 32 of the inner member 12 to cause translation of the inner member 12 with respect to the outer member 14. In a preferred embodiment, the gear member 16 includes a cylindrical cutout feature 76 extending around the inner wall 464 to cooperatively receive the lip 54 of the outer member 14. In this regard, the gear member 16 may rotate freely with respect to the outer member 14 while being retained from longitudinal and lateral movement. In a preferred embodiment, the gear member 16 also includes a series of cutouts 73 located proximate to the proximal end 68 for engaging a portion of a locking member.

With continued reference to FIGS. 6-7, the gear teeth 74 extend substantially from the proximal end 68 to the distal end 66 and extend around the entire periphery of at least a portion of the exterior wall 75. The outer-most external diameter 78 of the gear member 16 is sized to be the same as or slightly smaller than the smallest outer diameter of the endplates 20, 62 and the outer member 14. In this regard, when the implant 10 is viewed from the end in a plane perpendicular to the longitudinal axis 18, the gear member 16 does not protrude radially outward from beyond the perimeter of the endplates 20, 62.

As shown in FIG. 7, in a preferred embodiment, the gear teeth 74 extend a width 480 in a generally radial direction and generally extend radially outward to the outer diameter of the gear member 16. In this regard, the teeth 74 may be designed to have a width 480 to accommodate the expected gear forces given the particular gear ratio, types of material used, and desired overall diameter of prosthetic device 10. One skilled in the art will appreciate that the larger the outer diameter to which the teeth 74 radially extend, the larger the teeth 74 may be designed while still maintaining the same gear ratio. In this regard, when the teeth 74 are made larger, they generally have a better mechanical strength. Also, the ability to design larger, wider, and stronger teeth 74 is advantageous for embodiments where the implant 10 is made of PEEK, other plastic, or other non-metallic materials that may have less mechanical strength than, for instance, titanium.

Furthermore, as described in one embodiment, because the outer-most diameter of the gear member 16 may be as large as the outer diameter of the endplates 20, 62, and the teeth 74 extend radially to the outer-most diameter of the gear member 16, a larger inner diameter of the gear member 16 may be manufactured without compromising mechanical gear strength. As a result, a larger overall inner diameter of the implant 10 may be accommodated which allows the packing of more bone material therein and facilitates bone fusion once the implant 10 is implanted.

Figure 3:
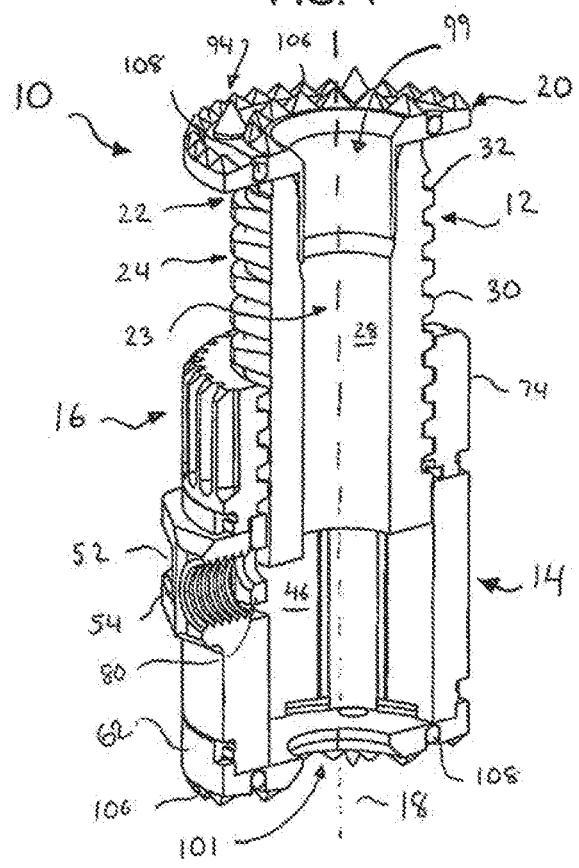
FIG. 3 is a cross-sectional view of the implant of FIG. 1 taken along line 3-3 of FIG. 1.
Figure 2:
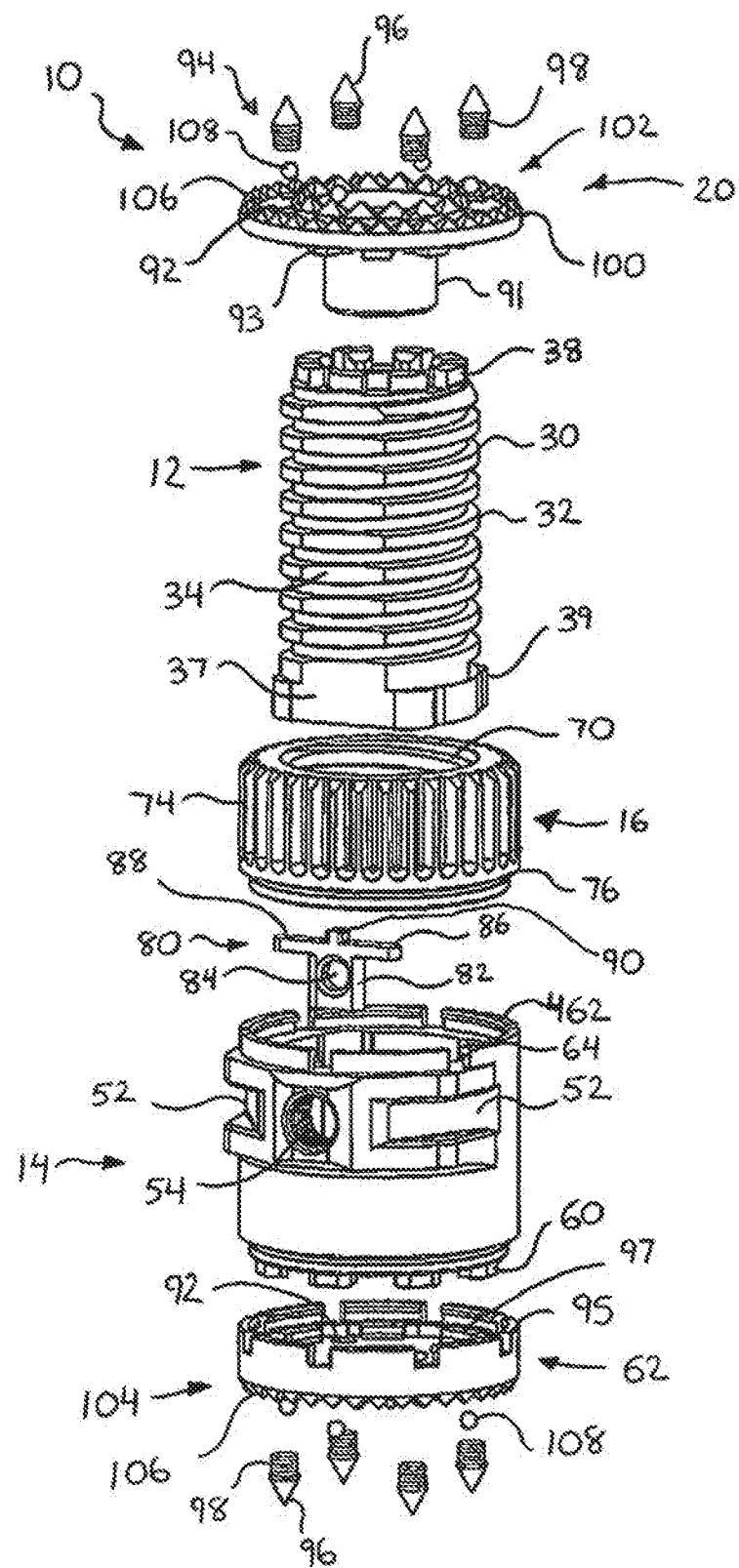
FIG. 2 is an exploded view of the implant of FIG. 1.
Figure 4:
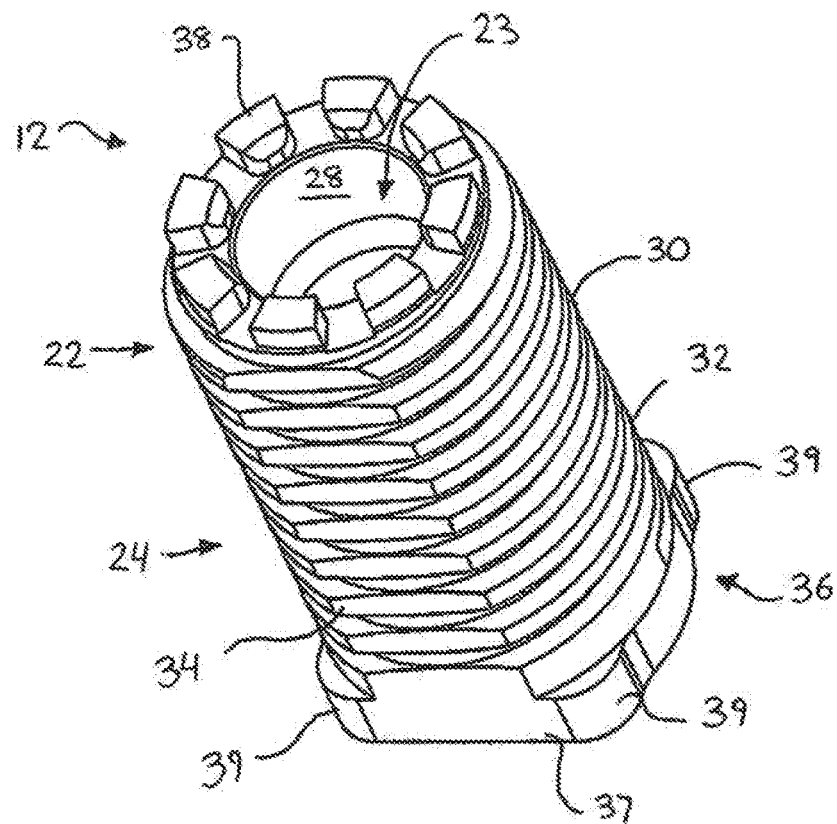
FIG. 4 is perspective view of an embodiment of an inner member of the implant of FIG. 1.

As seen in FIGS. 1-3, in a preferred embodiment, the teeth 74 are exposed to the exterior of prosthetic device 10. Because the teeth 74 are exposed around the periphery, little to no material is needed to cover up the exposed teeth, which generally makes the implant 10 lighter and easier to manufacture than prior art devices that require covering the gear teeth. In addition, the gear member 16 is more easily visible by a surgeon and more readily accessible by a rotation tool than devices that hide or cover gear teeth.

Referring to FIGS. 2, 5, and 7, in a preferred embodiment, the implant 10 also includes a locking member 80. The locking member 80 may be provided to substantially restrict all relative movement between inner member 12 and outer member 14, when, for example, the desired expansion of the prosthetic device 10 has been obtained. The locking member 80 has a body portion 82 with a through-hole 84. In a preferred embodiment, the body portion 82 has at least one, but preferably two, outwardly extending, flexible arms 86, 88 and at least one engagement member 90. In other preferred embodiments, instead of flexible arms 86, 88, it is contemplated that the locking member 80 may include an alternate biasing member, such as a leaf spring. The locking member 80 is configured and dimensioned to be received in the channel 57 of the outer member 14 in such a manner that the arms 86,88 rest against a shelf portion in the channel 57 and the through-hole 84 partially aligns with opening 54. The engagement member 90 preferably protrudes upwardly and is configured and dimensioned to engage the cutouts 73 of the gear member 16 to prevent the gear member 16 from rotating.

Referring now to FIGS. 1-3, in a preferred embodiment, the endplates 20, 62 are shown wherein the endplate 20 connects to the inner member 12 and endplate 62 connects to the outer member 14. In a preferred embodiment, endplate 20 includes an extension portion 91 which is received in the interior portion 23 of inner member 12, for example, in an interference or snap fit and includes a plurality of tabs 93 which interdigitate with tabs 38 to connect and position endplate 20 with respect to the inner member 12. Endplate 62 includes an extension portion 95 which engages the proximal end 44 of the outer member 14, for example, in an interference or snap fit and includes a plurality of tabs 97 which interdigitate with tabs 60 to connect and position endplate 62 with respect to the outer member 14. The endplates 20, 62 also preferably include hollow interior portions 99, 101 which are in fluid communication with the hollow interior portions 23, 50 of inner member 12 and outer member 14, respectively.

In a preferred embodiment, each endplate 20, 62 is generally annular in shape when viewed from the end or perpendicular to the longitudinal axis 18. It is, however, contemplated that the endplates 20, 62 can be other shapes including oblong, elliptical, kidney bean, polygonal, or geometric. Preferably, the endplates 20, 62 are designed to resemble or mimic the footprint of the vertebral body to which the endplates will engage. In this regard, endplates 20, 62 are configured to engage portions of the vertebrae in a predetermined orientation to maximize contact of the superior surface of the endplates 20, 62 with bone.

The dimensions of endplates 20, 62 can be varied to accommodate a patient's anatomy. In some embodiments, the endplates 20, 62 have a wedge-shaped profile to accommodate the natural curvature of the spine. In anatomical terms, the natural curvature of the lumbar spine is referred to as lordosis. When implant 10 is to be used in the lumbar region, the angle formed by the wedge should be approximately between 3.5 degrees and 16 degrees so that the wedge shape is a lordotic shape which mimics the anatomy of the lumbar spine. In alternate embodiments, the wedge shape profile may result from a gradual increase in height from an anterior side to a posterior side to mimic the natural curvature, kyphosis, in other regions of the spine. Thus, in other embodiments, the angle may be between about −4 degrees and −16 degrees.

As shown in FIGS. 1-3, in a preferred embodiment, the endplates 20, 40 include a plurality of mounting holes 92 spaced around the perimeter of each endplate 20, 40 for receiving insertable bone engaging members 94. In one embodiment, bone engaging members 94, comprise conical spikes 96 each having a cylindrical base portion 98 configured to fit within holes 92, for instance, by press-fit or by threaded engagement. In alternate embodiments, differently shaped bone engaging members 100 may be used, or in other embodiments no bone engaging members may be used. Referring again to FIG. 2, according to one embodiment, endplates 20, 62 have chamfered edges 100 around the perimeter to facilitate insertion and/or accommodate the shape of the vertebral bodies which they engage. The superior or bone engaging surfaces 102, 104 of endplates 20, 62 may also include numerous types of texturing to provide better initial stability and/or grasping contact between the end plate and the respective vertebrae. In a preferred embodiment, the texturing is a plurality of teeth 106. In preferred embodiments where the implant 10 is manufactured from PEEK or other plastic materials, the endplates 20, 62 may also include radio-opaque material, such as tantalum markers 108, which aid in providing location markers in radiographic images.

In preferred embodiments, the length, diameter, and shape of prosthetic device 10 may vary to accommodate different applications, different procedures, implantation into different regions of the spine, or size of vertebral body or bodies being replaced or repaired. For example, implant 10 may be expandable to a longer distance to replace multiple vertebral bodies. Also endplates 20, 62 can be sized and shaped as well as positioned to accommodate different procedures and approached to the spine. For example, endplates 20, 62 may be made smaller for smaller statured patients or for smaller regions of the cervical spine. In addition, it is not required that endplates 20, 62 be shaped and sized identically and in alternate embodiments they can be shaped or sized differently than each other and/or include different bone engaging members or texturing.

Figure 8:
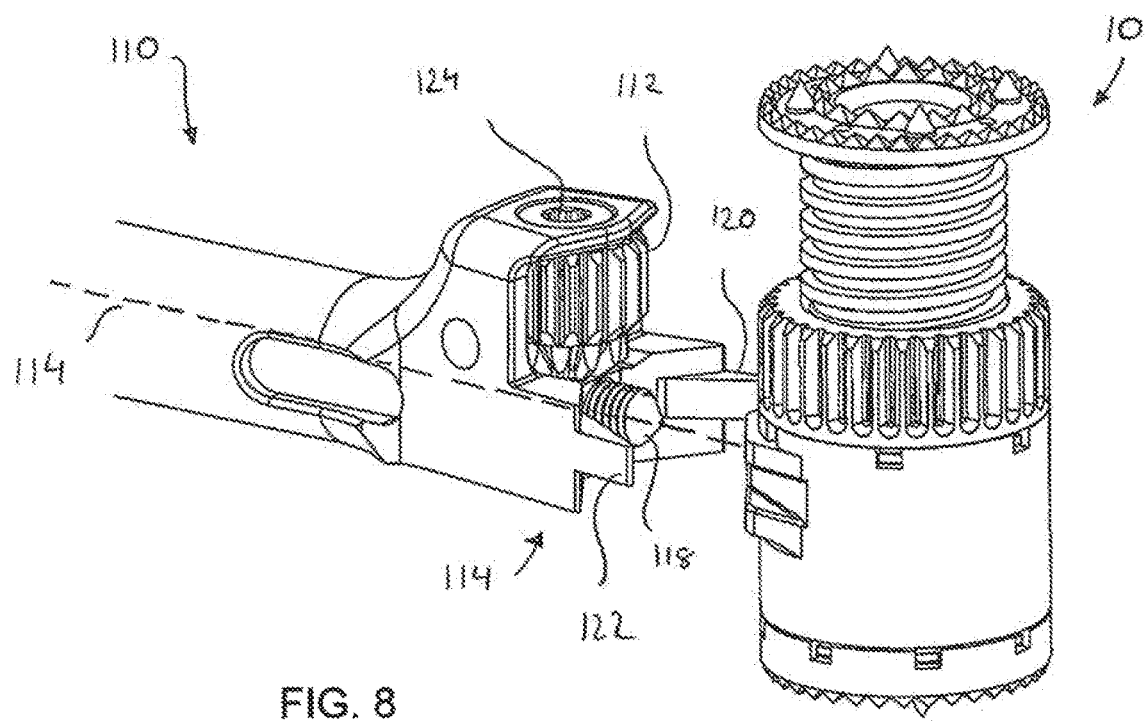
FIG. 8 is a perspective of one embodiment of a tool according to the present invention.
Figure 9:
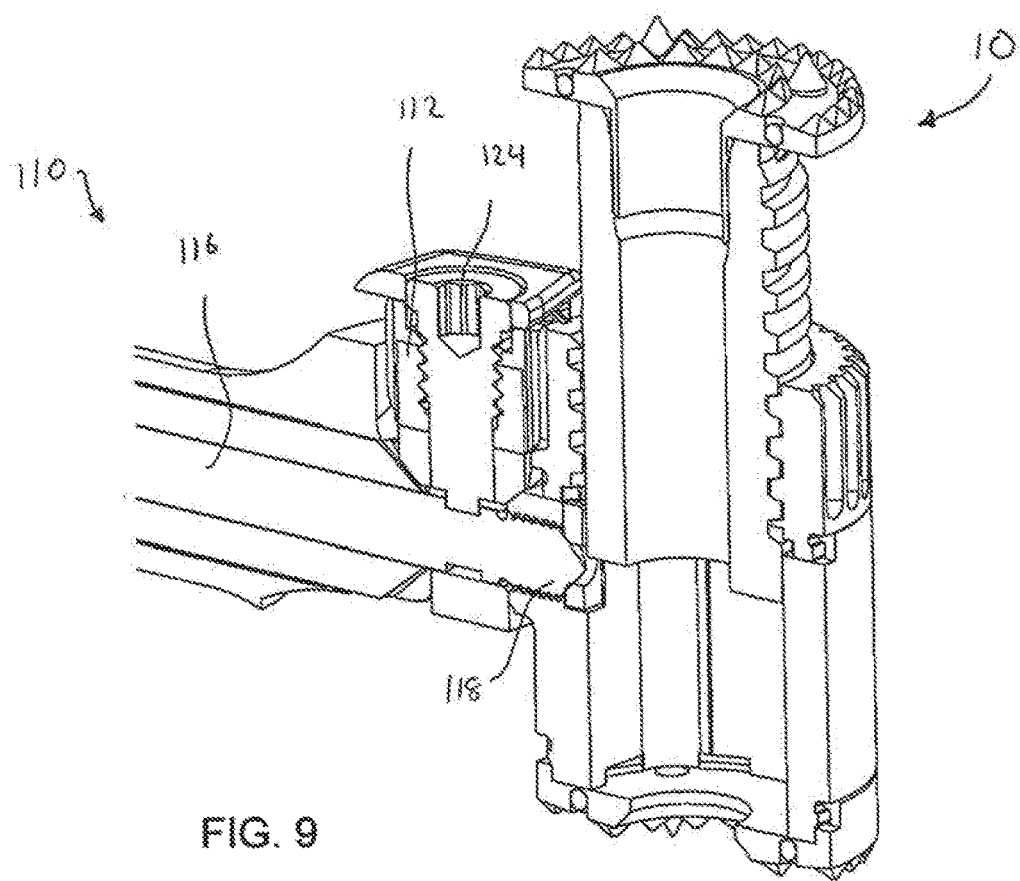
FIG. 9 is a cross-sectional view of the tool of FIG. 8 shown engaging an embodiment of an expandable implant according to the present invention.
Figure 10:
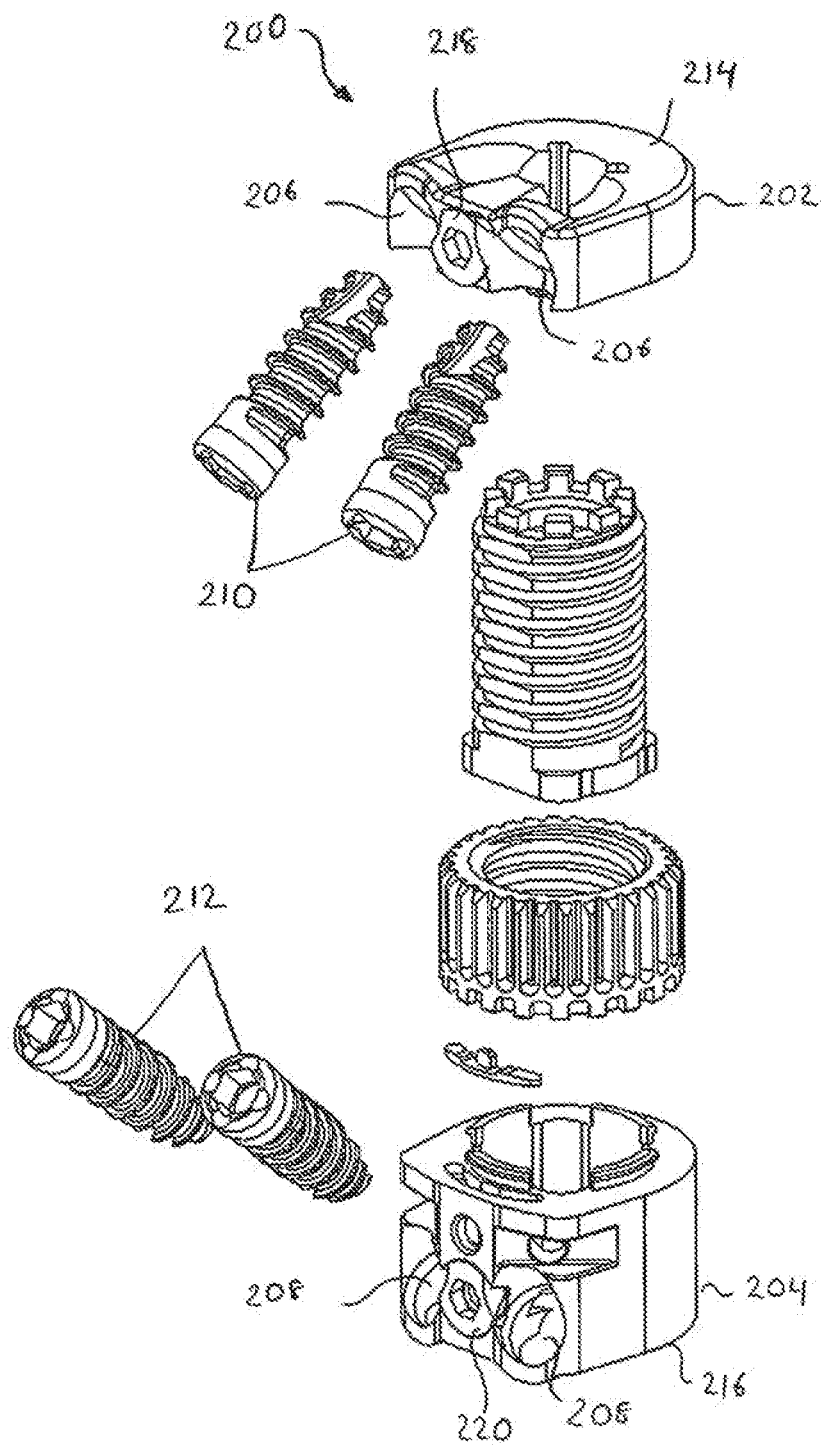
FIG. 10 is a perspective view of another embodiment of an implant according to the present invention.

Turning now to FIGS. 8-9, the implant 10 may be expanded by a tool 110 that includes a gear member 112 at its distal end 114. The tool 110 extends along a tool axis 114 and in operation the tool 110 is configured to engage the implant 10 such that the tool axis 114 is generally perpendicular to the longitudinal axis 18. The gear member 112 is configured to engage teeth 74 of the gear member 16 such that when the gear member 112 is rotated about the axis of the tool 110, the gear member 16 of the implant 10 is rotated about the longitudinal axis 18 and the inner member 12 translates along the longitudinal axis 18 to either expand or contract the implant 10. In a preferred embodiment, the tool 110 may include a central shaft 116 having a threaded distal tip portion 118 that extends distally beyond gear member 112 to facilitate location and mounting of tool 110 with the implant 10. The threaded distal tip portion 118 preferably includes a generally conical end portion and may be configured to extend radially through the opening 54 and threadably engage opening 54 in the outer member 14.

With continued reference to FIGS. 8-9, in one embodiment of prosthetic device 10 at least one, but preferably a plurality of mounting features or slots 52 are provided along the outer surface 48 of outer member 14. The tool 110 includes at least one, but preferably two, articulating arms 120, 122 that engage slots 52 for better engagement of the tool 110 with the implant 10 during insertion of the implant 10. In another preferred embodiment, the tool 110 may include arms 120, 122 that do not articulate.

In an exemplary use of the tool 110 with the implant 10, the tool 110 initially engages the slots 52 of the implant 10 via the arms 120, 122 and gear member 112 engages gear member 16 via their respective interdigitating teeth. A control member on the proximal end of the tool 110 (not shown) is manipulated to advance the central shaft 116 toward opening 54. The threaded tip portion 118 enters into opening 54 engaging the threads in opening 54 as well as engaging the through-hole 84 of locking member 80. It is also contemplated that the central shaft 116 is not movable with respect to the tool 110. In that embodiment, the entire tool 110 is moved so that the central shaft can enter and engage the opening 54 and the through-hole 84. As discussed earlier, the though-hole 84 is offset from opening 54, thus, when threaded tip 118 engages and advances into the opening 54 and the through-hole 84, the locking member 80 is pulled downwardly, riding along the conical edge of the tip 118 until the through-hole 84 is aligned with the opening 54. As the locking member 80 is pulled downwardly, the arms 82, 84 are flexed and the engagement member 90 disengages from the cutout 73 of the gear member 16 allowing the gear member 16 to rotate freely. The gear member 112 of tool 110 is then rotated via opening 114 which, in turn, rotates gear member 16. As discussed above, the rotation of gear member 16 results in the movement of inner member 12 causing the implant 10 to either expand or contract, depending on the direction the gear member 16 is rotated. Once the desired height for implant 10 is achieved, the tool member 110 is disengaged from implant 10. When the tool 110 is removed, the locking member 80 returns to the back to its initial position because of the arms 82, 84 returning back to their unflexed, at-rest state. The initial position of locking member 80 prevents the gear member 16 from turning because of the engagement of engagement member 90 with the cutouts 73. In that regard, implant 10 is locked from movement when the locking member 80 is in its initial position.

The benefit provided by the present locking mechanism is that it allows for a positive lock that engages and disengages automatically with the engagement and disengagement of the tool 110 with the implant 10, which minimizes the steps the surgeon must perform during the procedure.

Referring now to FIGS. 10-13, alternate preferred embodiments of endplates for the expandable implant 10 are shown. Looking at FIG. 10, in one variation, the endplates 202 and outer member 204 each include at least one screw hole 206, 208, but, preferably, each include two screw holes. The screw holes 206, 208 are configured and dimensioned to receive screws 210, 212. In a preferred embodiment, the screw holes 206, 208 are angled such that when the screws 210, 212 are seated in the screw holes 206, 208, the screws 210, 212 will extend outwardly from the superior surface 214 of endplate 202 and inferior surface 216 of outer member 204. Endplate 202 and outer member 204 also preferably include a locking element 218, 220 which, in a first position, allow the screws 210, 212 to back out from the seated position and, in a second position, block the screws 210, 212 from backing out of the seated position. In an exemplary use, once the implant 200 is installed and expanded to the desired position, the screws 210, 212 can be installed through the screw holes 206, 208 in such a manner as to purchase into the adjacent vertebral bodies. Once the screws 210, 212 are properly installed, including being engaged with the adjacent vertebral bodies, the locking elements 218, 220 can be actuated to block the screws 210, 212 from backing out of their installed position. The inclusion of screws 210, 212 in the endplate 202 and the outer member 204 provides for additional fixation of the implant 200 in the intervertebral space.

Figure 11:
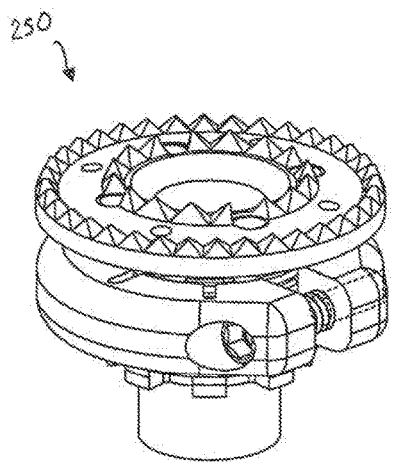
FIG. 11 is a perspective view of another embodiment of an endplate of an implant according to the present invention.
Figure 12:
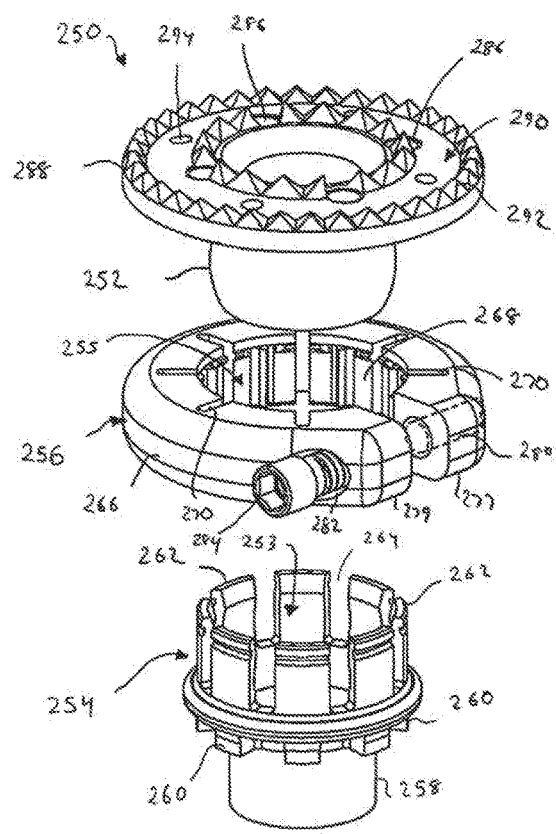
FIG. 12 is an exploded view of the endplate of FIG. 11.
Figure 13:
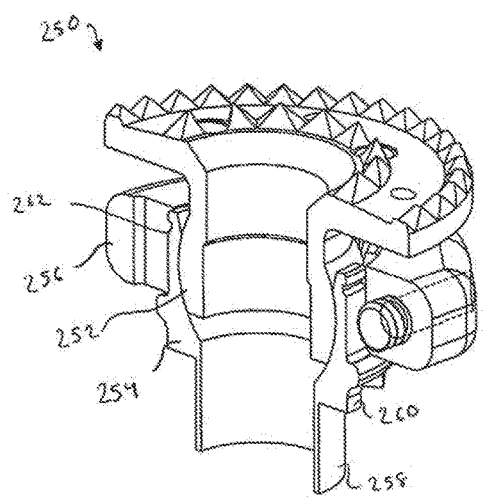
FIG. 13 is a cross-sectional view of the endplate of FIG. 11.

Turning to FIGS. 11-13, another preferred embodiment of an endplate 250 is shown. The endplate 250 is similar to endplate 20 but includes the additional functionality of being poly-axially rotatable with respect to an implant. In a preferred embodiment, endplate 250 includes a generally arcuate extension portion 252 which is received in an interior portion 253 of a receiving member 254 in such a manner as to allow the endplate 250 to move poly-axially with respect to the receiving member 254.

In a preferred embodiment, the receiving member 254 is received in an interior portion 255 of a locking ring 256. The receiving member 254 preferably includes a neck portion 258 as well as a plurality of tabs 260. The neck portion 258 is configured and dimensioned to be received within a hollow interior of an inner member, for example, in an interference or snap fit, and the plurality of tabs 260 interdigitate with tabs to connect and position the receiving member 254 with respect to an inner member. The receiving member 254 further includes a plurality of fingers 262 configured to cooperatively receive the extension portion 252 of endplate 250. A plurality of relief spaces or slots 264 are radially spaced between fingers 262 to allow fingers 262 to bend or flex radially.

In a preferred embodiment, the locking ring 256 has a generally annular, c-shape and includes an exterior wall 266, an interior wall 268, and ends 277, 279. The interior wall 268 preferably defines and interior portion 255. In a preferred embodiment, the interior wall 268 includes a plurality of channel 270 which are spaced radially along the locking ring 256. The channels 270 allow the locking ring 256 to bend or flex radially. The ends 277, 279 each include openings 280, 282 which may be partially threaded. A locking element 284 is configured and dimensioned to be threadingly received in the openings 280, 282. It also contemplated that that locking element 284 can engage the ends 277, 279 by other non-threaded means, such as a sliding fit.

With continued reference to FIGS. 11-13, in a preferred embodiment, the endplate 250 includes a plurality of mounting holes 286 spaced around the perimeter of the endplate 250 for receiving insertable bone engaging members. In one embodiment, bone engaging members, comprise conical spikes each having a cylindrical base portion configured to fit within holes 286, for instance, by press-fit or by threaded engagement. In alternate embodiments, differently shaped bone engaging members may be used, or in other embodiments no bone engaging members may be used. According to one preferred embodiment, endplate 250 has chamfered edges 288 around the perimeter to facilitate insertion and/or accommodate the shape of the vertebral bodies which they engage. The superior or bone engaging surfaces 290 of endplate 250 may also include numerous types of texturing to provide better initial stability and/or grasping contact between the end plate and the respective vertebrae. In a preferred embodiment, the texturing is a plurality of teeth 292. In preferred embodiments where the implant is manufactured from PEEK or other plastic materials, the endplate 250 may also include radio-opaque material, such as tantalum markers 294, which aid in providing location markers in radiographic images.

In an exemplary use, during the implant installation and expansion to the desired position, the endplate 250 can move in poly-axial fashion with respect to the implant to accommodate the anatomy of the adjacent vertebral body as well as accommodate the natural curvature of the spine, such as kyphosis and lordosis. More specifically, the arcuate extension portion 252 is free to move in the interior portion 253 of the receiving portion 254. The fingers 262 are generally compliant and can flex to accommodate the movement of the arcuate extension portion 252. Once the desired positioning of the endplate 250 is achieved, the endplate 250 can be locked in place. The endplate 250 is locked in place by actuating the locking element 284. As the element 284 engages the threading in opening 280,282 the ends 277, 279 of the locking ring 256 are brought closer together contracting the ring 254 and reducing the size of the interior portion 255. As the ring 254 contracts, the fingers 262 of the receiving member 254, abutting against the inner wall 268, are flexed radially inwardly pushing against the extension portion 252. As a result, the endplate 250 is locked in place.

Referring to FIGS. 14-19, another preferred embodiment of an expandable vertebral implant 300 is shown. The implant 300 preferably comprises an inner member 302 which may be telescopingly received within an outer member 304. The implant 300 further comprises a gear member 306 generally configured to effect translation of the inner member 302 with respect to the outer member 304 thereby allowing for expansion and contraction of the implant 300. The inner member 302, the outer member 304, and the gear member 306 are preferably centered along a longitudinal axis 308 and define a hollow interior portion which may be filled with bone material, bone growth factors, bone morphogenic proteins, or other materials for encouraging bone growth, blood vessel growth or growth of other tissue through the many apertures in the device. In one preferred embodiment, members 302, 304, and 306 are made of a polyether ether ketone (PEEK) plastic material. There are several known advantages of PEEK plastic material including being radiolucent, having a mechanical strength that is close to bone, and may be more easily sterilized than other plastics. In alternate preferred embodiments, the members 302, 304, and 306 may be made of a biologically inert metal alloys, such as titanium, or other suitable materials.

Referring to FIGS. 14-19, the inner member 302 has a generally cylindrical body 314 with a distal end 312 and a proximal end 326. In a preferred embodiment, the body 314 of the inner member 302 comprises an inner surface 318 and an outer surface 320 and generally defines a hollow interior portion 313 extending axially therethrough. At least part of the outer surface 320 preferably includes external threads 322. Located proximate to the distal end 312 of the body 314 are a plurality of tabs 328 which assist in connecting and positionally locating an endplate 310. In a preferred embodiment, the body 314 is configured and dimensioned to be cooperatively received within outer member 304.

Figure 15:
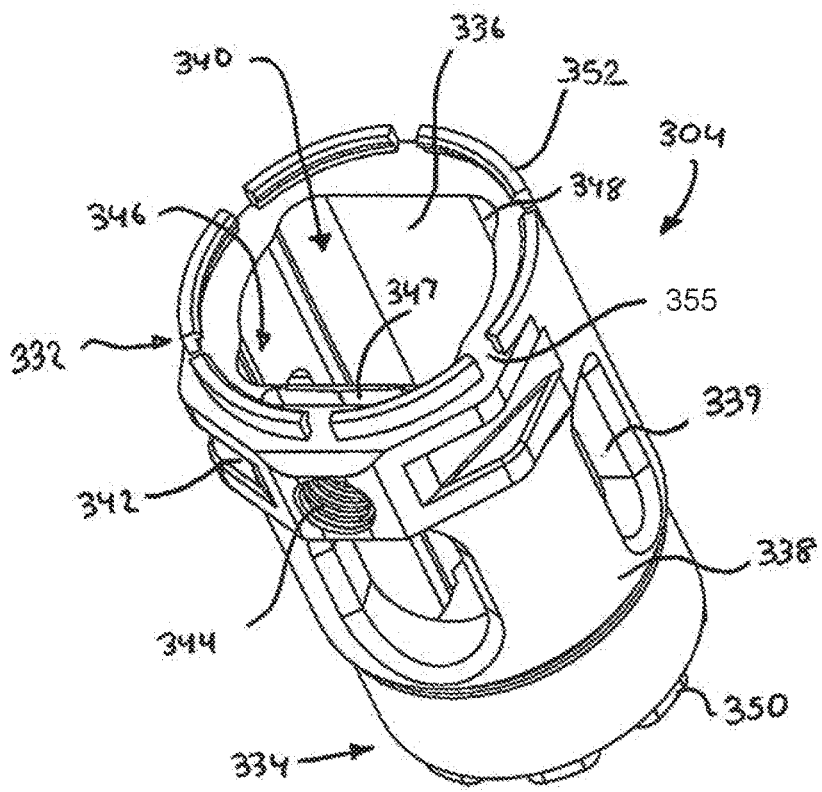
FIG. 15 is perspective view of an embodiment of an outer member of the implant of FIG. 14.

The outer member 304 has a generally cylindrical body 330 with a distal end 332 and a proximal end 334. In a preferred embodiment, the body 330 of the outer member 304 comprises an inner surface 336 and an outer surface 338 and generally defines a hollow interior portion 340 extending axially therethrough. In one preferred embodiment, extending from the outer surface 338 through the inner surface 336 is at least one opening 339 configured and dimensioned to allow access to the hollow interior portion 340. Opening 339 can be used as an access to pack the outer member 304 with bone growth material. The outer surface 338 preferably has at least one slot 342 and an opening 344 configured and dimensioned to receive a portion of an implantation tool. In a preferred embodiment, the opening 344 extends from the outer surface 338 to the hollow interior portion 340 and at least a portion of the opening 344 is threaded. As best seen in FIG. 15, the inner surface 336 includes a channel 347 for receiving a locking member (discussed below). Located proximate to the proximal end 334 of the outer member 304 are a plurality of tabs 350 which assist in connecting and positionally locating an endplate 352. In a preferred embodiment, a lip 352 is formed around the exterior of the distal end 332 of body 330 and is configured to cooperatively fit with a portion of the gear member 306. A plurality of relief spaces or slots 354 are radially spaced around lip 352 to facilitate a snapping engagement of the lip 352 with the gear member 306. In this regard, slots 354 allow the lip 352 to deform slightly and contract in the radial direction to accommodate gear member 306 to snap on to lip 352. In a preferred embodiment, the interior portion 340 of body 330 is configured and dimensioned to cooperatively receive body 314 of inner member 302 within outer member 304. In this regard, the dimensions of interior portion 340 of body 330 are greater than dimensions of body 314 of inner member 302.

Figure 14:
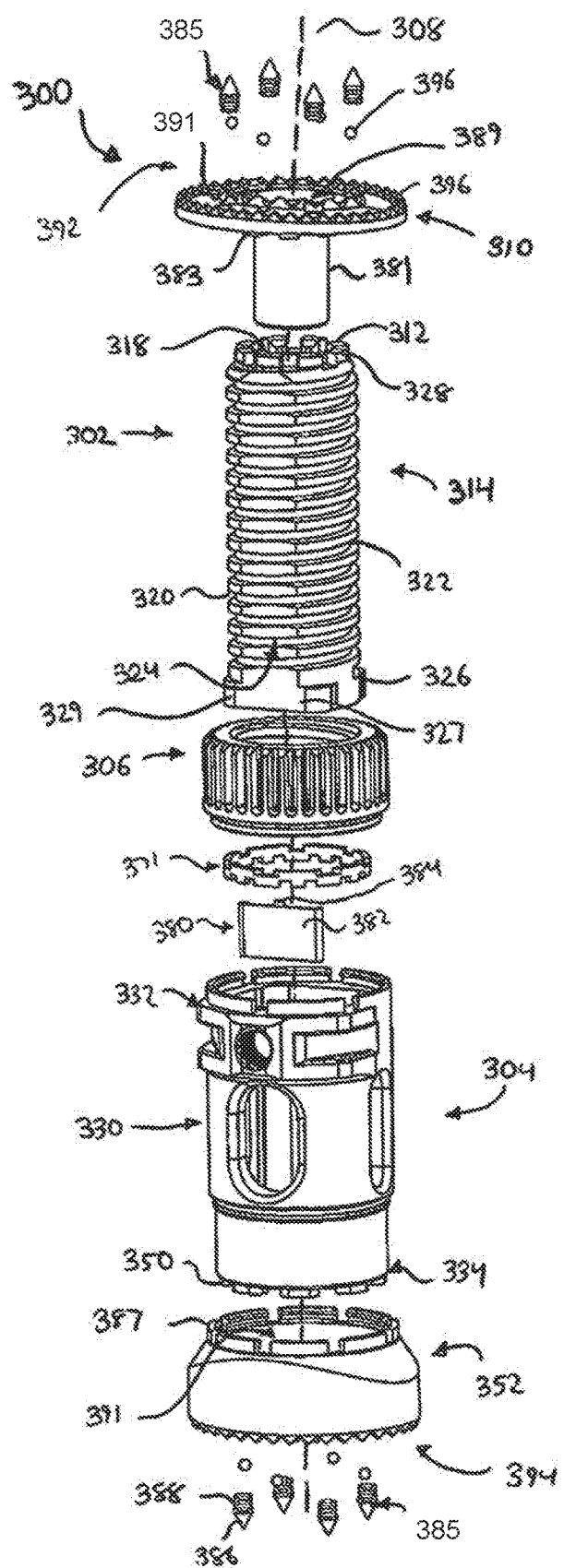
FIG. 14 is an exploded view of another embodiment of an implant according to the present invention.
Figure 19:
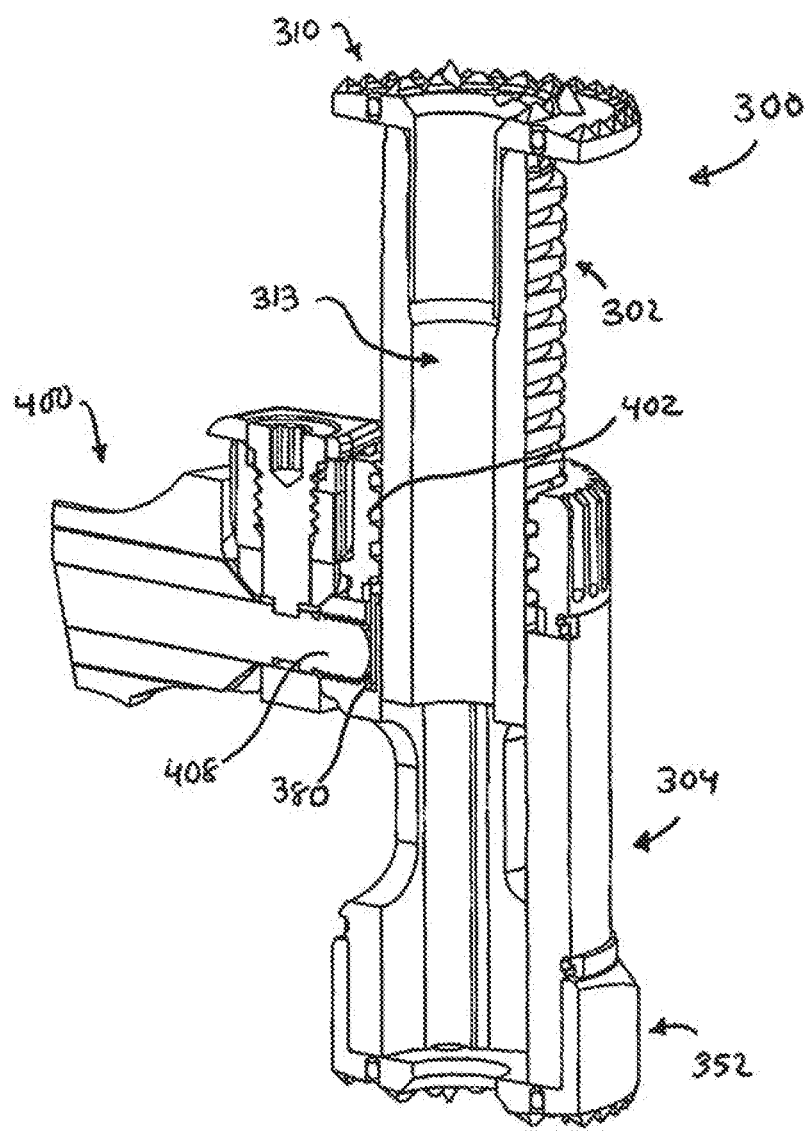
FIG. 19 is a cross-sectional view of the tool of FIG. 18 shown engaging an embodiment of an expandable implant according to the present invention.

As best seen in FIGS. 14, 15, and 19, in a preferred embodiment of a prosthetic device 300, the body 314 of the inner member 312 includes a flattened portion 324 which extends at least in part from the distal end 312 to the proximal end 326 and includes a base member 327 having at least one lobe 329 located proximate to the distal end 326 of the body 314. Focusing on FIG. 15, the body 330 of the outer member 304 includes a flattened area 346 and at least one depression 348 on the inner surface 336. When the inner member 302 is assembled within the outer member 304, the flattened area 346 of the outer member 304 cooperatively aligns with the flattened portion 324 of the inner member 302 and the at least one depression 348 of outer member 304 receives the at least one lobe 329 of the inner member 302. The flattened portion 324 and the flattened area 346 along with the lobes 329 and the depressions 348 cooperate to allow the inner member 302 to linearly move with respect to the outer member 304 but prevent the inner member 302 from rotating with respect to the outer member 304. In addition, the base member 327 serves as a stop preventing the inner member 302 from rotating to a point of disengagement from outer member 304.

Figure 16:
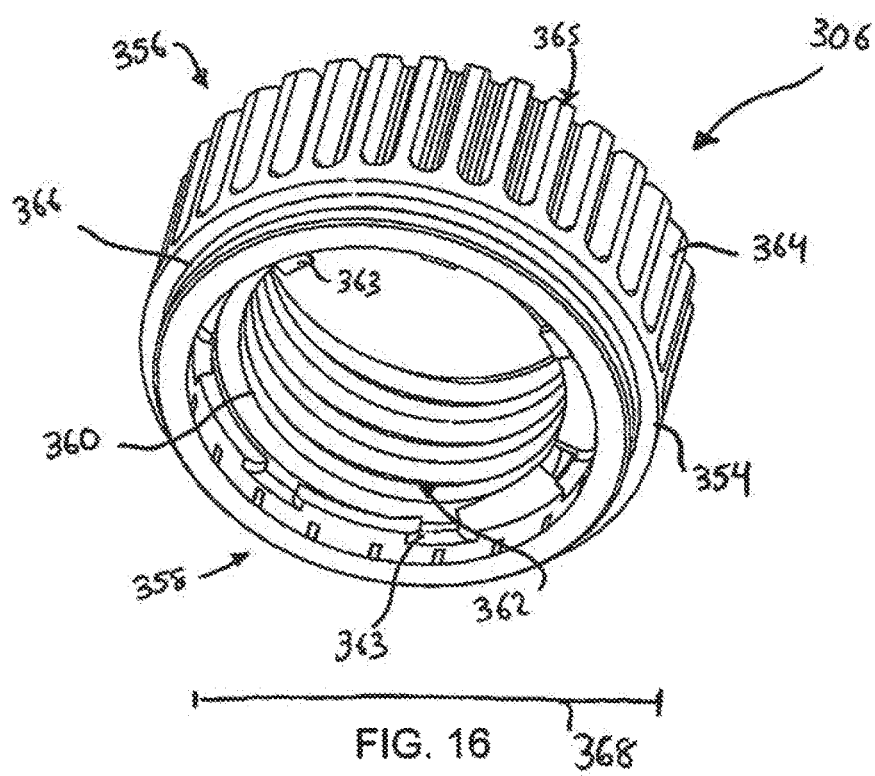
FIG. 16 is a perspective view of one embodiment of a gear member of the implant of FIG. 14.
Figure 17:
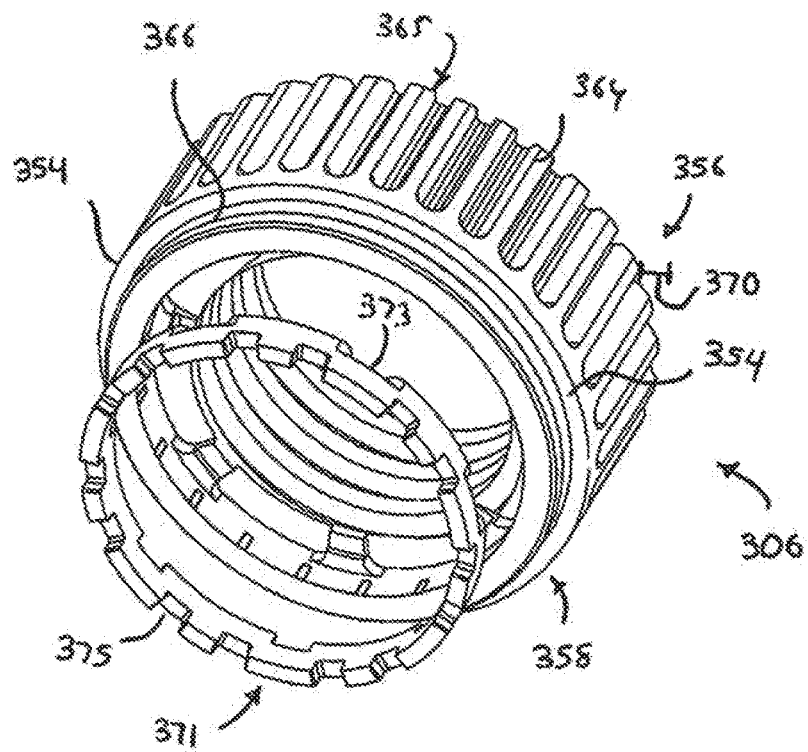
FIG. 17 is a perspective view of one embodiment of a gear member with an engagement element of the implant of FIG. 14.

Referring now to FIGS. 16-17, a gear member 306 comprises a generally hollow body 354 extending from a distal end 356 to a proximal end 358 with a helical thread 360 along at least part of an inner wall 362 and an array of gear teeth 364 along a portion of the exterior wall 365. The gear member 16 is generally configured to rotatably connect to the distal end 332 of the outer member 304 and the internal helical thread 360 is configured to engage the external threads 322 of the inner member 302 to cause translation of the inner member 302 with respect to the outer member 304. In a preferred embodiment, the gear member 306 includes a cylindrical cutout feature 366 extending around the inner wall 354 to cooperatively receive the lip 352 of the outer member 304. In this regard, the gear member 306 may rotate freely with respect to the outer member 304 while being retained from longitudinal and lateral movement. In a preferred embodiment, the gear member 306 also includes a series of engagement members 363 located proximate to the proximal end 358 for engaging a portion of a locking ring 371. In a preferred embodiment, the locking ring 371 is configured and dimensioned to be received in the gear member 306 and includes a plurality of slots 373 for engaging the engagement member 363 on a first end and includes a series of cutouts 375 for engaging a locking member on a second end. The engagement members 363 fit within the slots 373 in such a manner as to prevent the locking ring 371 from disengaging from the gear member 306. In one preferred embodiment, the locking ring 371 may be made of a different material than the gear member 306. For example, the locking ring may be made from titanium or other biocompatible metal and the gear member may be made from PEEK or other biocompatible polymer material.

With continued reference to FIGS. 16-17, the gear teeth 364 extend substantially from the proximal end 358 to the distal end 356 and extend around the entire periphery of at least a portion of the exterior wall 365. The outer-most external diameter 368 of the gear member 306 is sized to be the same as or slightly smaller than the smallest outer diameter of the endplates 310, 352 and the outer member 304. In this regard, when the implant 300 is viewed from the end in a plane perpendicular to the longitudinal axis 308, the gear member 306 does not protrude radially outward from beyond the perimeter of the endplates 310, 352.

As shown in FIG. 17, in a preferred embodiment, the gear teeth 364 extend a width 370 in a generally radial direction and generally extend radially outward to the outer diameter of the gear member 306. In this regard, the teeth 364 may be designed to have a width 370 to accommodate the expected gear forces given the particular gear ratio, types of material used, and desired overall diameter of prosthetic device 300. One skilled in the art will appreciate that the larger the outer diameter to which the teeth 364 radially extend, the larger the teeth 364 may be designed while still maintaining the same gear ratio. In this regard, when the teeth 364 are made larger, they generally have a better mechanical strength. Also, the ability to design larger, wider, and stronger teeth 364 is advantageous for embodiments where the implant 300 is made of PEEK, other plastic, or other non-metallic materials that may have less mechanical strength than, for instance, titanium.

Furthermore, as described in one embodiment, because the outer-most diameter of the gear member 306 may be as large as the outer diameter of the endplates 310, 352, and the teeth 364 extend radially to the outer-most diameter of the gear member 306, a larger inner diameter of the gear member 306 may be manufactured without compromising mechanical gear strength. As a result, a larger overall inner diameter of the implant 300 may be accommodated which allows the packing of more bone material therein and facilitates bone fusion once the implant 300 is implanted.

As seen in FIG. 14, in a preferred embodiment, the teeth 364 are exposed to the exterior of prosthetic device 300. Because the teeth 364 are exposed around the periphery, little to no material is needed to cover up the exposed teeth, which generally makes the implant 300 lighter and easier to manufacture than prior art devices that require covering the gear teeth. In addition, the gear member 306 is more easily visible by a surgeon and more readily accessible by a rotation tool than devices that hide or cover gear teeth.

Figure 18:
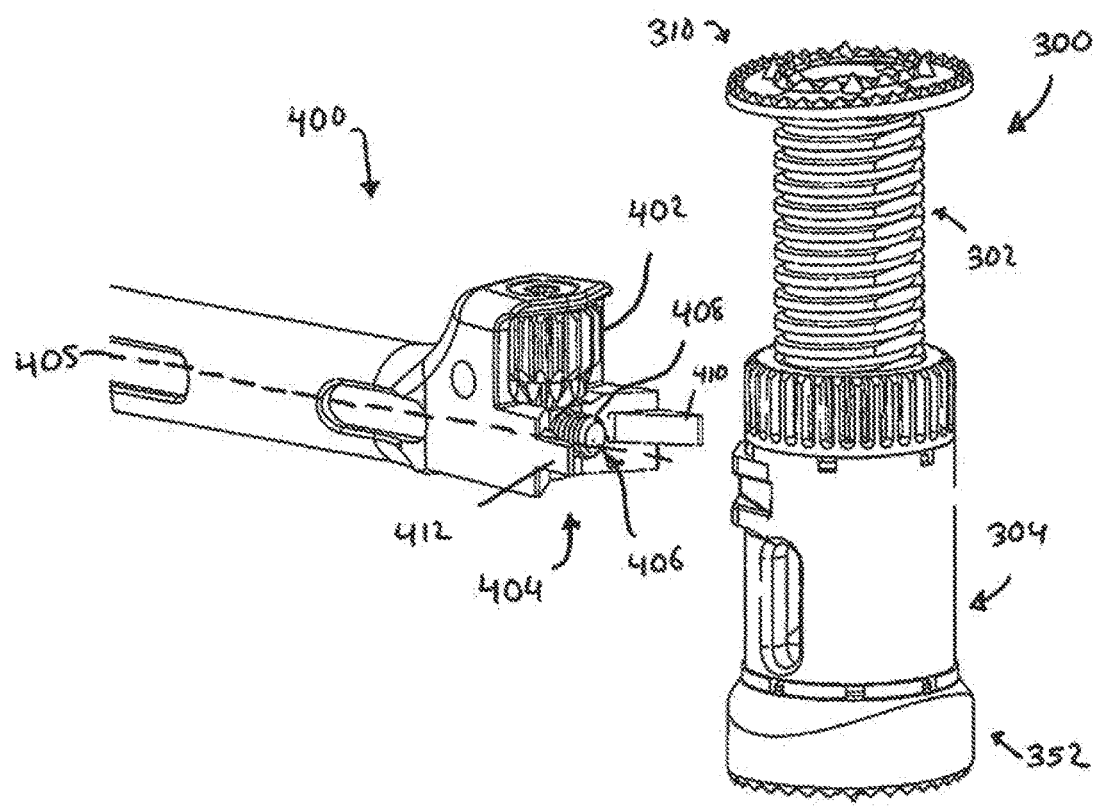
FIG. 18 is a perspective of one embodiment of a tool according to the present invention.

Referring to FIGS. 14, 18, and 19, in a preferred embodiment, the implant 300 also includes a locking member 380. The locking member 380 may be provided to substantially restrict all relative movement between inner member 302 and outer member 304, when, for example, the desired expansion of the prosthetic device 300 has been obtained. The locking member 380 has a body portion 382 with an engagement member 384. In a preferred embodiment, the body portion 382 is dimensioned to be flexible allowing the locking member 380 to flex but return to its original configuration or orientation. The locking member 380 is configured and dimensioned to be received in the channel 347 of the outer member 304 in such a manner that body portion 382 aligns with opening 344. The engagement member 384 preferably protrudes upwardly and is configured and dimensioned to engage the cutouts 375 of the locking ring 371, which is fixed to the gear member 306, to prevent the gear member 306 from rotating.

Referring now to FIG. 14, in a preferred embodiment, the endplates 310, 352 are shown wherein the endplate 310 connects to the inner member 302 and endplate 352 connects to the outer member 304. In a preferred embodiment, endplate 310 includes an extension portion 381 which is received in the interior portion 313 of inner member 302, for example, in an interference or snap fit and includes a plurality of tabs 383 which interdigitate with tabs 328 to connect and position endplate 310 with respect to the inner member 302. Endplate 352 includes a plurality of tabs 387 which interdigitate with tabs 350 to connect and position endplate 352 with respect to the outer member 304. The endplates 310, 352 also preferably include hollow interior portions 389, 391 which are in fluid communication with the hollow interior portions 313, 340 of inner member 302 and outer member 304, respectively.

In a preferred embodiment, each endplate 310, 352 is generally annular in shape when viewed from the end or perpendicular to the longitudinal axis 308. It is, however, contemplated that the endplates 310, 352 can be other shapes including oblong, elliptical, kidney bean, polygonal, or geometric. Preferably, the endplates 310, 352 are designed to resemble or mimic the footprint of the vertebral body to which the endplates will engage. In this regard, endplates 310, 352 are configured to engage portions of the vertebrae in a predetermined orientation to maximize contact of the superior surface of the endplates 310, 352 with bone.

The dimensions of endplates 310, 352 can be varied to accommodate a patient's anatomy. In some embodiments, the endplates 310, 352 have a wedge-shaped profile to accommodate the natural curvature of the spine. In anatomical terms, the natural curvature of the lumbar spine is referred to as lordosis. When implant 300 is to be used in the lumbar region, the angle formed by the wedge should be approximately between 3.5 degrees and 16 degrees so that the wedge shape is a lordotic shape which mimics the anatomy of the lumbar spine. In alternate embodiments, the wedge shape profile may result from a gradual increase in height from an anterior side to a posterior side to mimic the natural curvature, kyphosis, in other regions of the spine. Thus, in other embodiments, the angle may be between about −4 degrees and −16 degrees.

As shown in FIG. 14, in a preferred embodiment, the endplates 310, 330 include a plurality of mounting holes 391 spaced around the perimeter of each endplate 310, 330 for receiving insertable bone engaging members 385. In one embodiment, bone engaging members 384, comprise conical spikes 386 each having a cylindrical base portion 388 configured to fit within holes 391, for instance, by press-fit or by threaded engagement. In alternate embodiments, differently shaped bone engaging members 385 may be used, or in other embodiments no bone engaging members may be used. Referring again to FIG. 14, according to one embodiment, endplates 310, 352 have chamfered edges around the perimeter to facilitate insertion and/or accommodate the shape of the vertebral bodies which they engage. The superior or bone engaging surfaces 392, 394 of endplates 310, 352 may also include numerous types of texturing to provide better initial stability and/or grasping contact between the end plate and the respective vertebrae. In a preferred embodiment, the texturing is a plurality of teeth 396. In preferred embodiments where the implant 10 is manufactured from PEEK or other plastic materials, the endplates 310, 352 may also include radio-opaque material, such as tantalum markers 398, which aid in providing location markers in radiographic images.

In preferred embodiments, the length, diameter, and shape of prosthetic device 300 may vary to accommodate different applications, different procedures, implantation into different regions of the spine, or size of vertebral body or bodies being replaced or repaired. For example, implant 300 may be expandable to a longer distance to replace multiple vertebral bodies. Also endplates 310, 352 can be sized and shaped as well as positioned to accommodate different procedures and approached to the spine. For example, endplates 310, 352 may be made smaller for smaller statured patients or for smaller regions of the cervical spine. In addition, it is not required that endplates 310, 352 be shaped and sized identically and in alternate embodiments they can be shaped or sized differently than each other and/or include different bone engaging members or texturing.

Turning now to FIGS. 18-19, the implant 300 may be expanded by a tool 400 that includes a gear member 402 at its distal end 404. The tool 400 extends along a tool axis 405 and in operation the tool 400 is configured to engage the implant 300 such that the tool axis 405 is generally perpendicular to the longitudinal axis 308. The gear member 402 is configured to engage teeth 364 of the gear member 306 such that when the gear member 402 is rotated, the gear member 402 of the implant 400 is rotated about the longitudinal axis 18 and the inner member 302 translates along the longitudinal axis 308 to either expand or contract the implant 300. In a preferred embodiment, the tool 400 may include a central shaft 406 having a threaded distal tip portion 408 that extends distally beyond gear member 402 to facilitate location and mounting of tool 400 with the implant 300. The threaded distal tip portion 408 preferably includes a generally conical end portion and may be configured to extend radially through the opening 344 and threadably engage opening 344 in the outer member 304.

With continued reference to FIGS. 18-19, in one embodiment of prosthetic device 300 at least one, but preferably a plurality of mounting features or slots 342 are provided along the outer surface 338 of outer member 304. The tool 400 includes at least one, but preferably two, arms 410, 412 that engage slots 342 for better engagement of the tool 400 with the implant 300 during insertion of the implant 300. In another preferred embodiment, the tool 400 may include arms 410, 412 that articulate.

In an exemplary use of the tool 400 with the implant 300, the tool 400 initially engages the slots 342 of the implant 300 via the arms 410, 412 and gear member 402 engages gear member 306 via their respective interdigitating teeth. A control member on the proximal end of the tool 400 (not shown) is manipulated to advance the central shaft 406 toward opening 344. The threaded tip portion 408 enters into opening 344 engaging the threads in opening 344 as well as engaging the body 382 of locking member 380. It is also contemplated that the central shaft 406 is not movable with respect to the tool 400. In that embodiment, the entire tool 400 is moved so that the central shaft can enter and engage the opening 344 and the body 382. When threaded tip portion 408 engages and advances into the opening 344 and pushes against body 382 of the locking member 380, the locking member 380 is flexed inwardly toward the center of the implant 300. As the locking member 380 flexes inwardly, the engagement member 384 disengages from the cutout 375 of the locking ring 371, which is fixed to the gear member 306, allowing the gear member 306 to rotate freely. The gear member 402 of tool 400 is then rotated which, in turn, rotates gear member 306. As discussed above, the rotation of gear member 306 results in the movement of inner member 302 causing the implant 300 to either expand or contract, depending on the direction the gear member 306 is rotated. Once the desired height for implant 300 is achieved, the tool member 400 is disengaged from implant 300. When the tool 400 is removed, the locking member 380 returns to the back to its initial position because the threaded tip portion 408 is no longer pushing against the body 382 of the locking member 380 causing it to flex inwardly. The initial position of locking member 380 prevents the gear member 306 from turning because of the engagement of engagement member 384 with the cutouts 375 of the locking ring 371. In that regard, implant 300 is locked from movement when the locking member 380 is in its initial position.

The benefit provided by the present locking mechanism is that it allows for a positive lock that engages and disengages automatically with the engagement and disengagement of the tool 400 with the implant 300, which minimizes the steps the surgeon must perform during the procedure While the invention herein disclosed has been described by means of specific embodiments and applications thereof, numerous modifications and variations can be made thereto by those skilled in the art without departing from the scope of the invention as set forth in the claims.

What is claimed is:

1. An expandable prosthetic implant for engagement between vertebrae, comprising:
   an inner member having an upper end and a lower end, a hollow interior portion, a threaded external portion extending along the inner member from the upper end toward the lower end, and at least one protrusion which extends outwardly from the lower end of the inner member, wherein the at least one protrusion is positioned below the threaded external portion when the prosthetic implant is in an expanded configuration;

an outer member having a hollow interior portion configured to coaxially receive the inner member therein, the outer member including a groove, wherein the inner and outer members are moveable relative to each other along a longitudinal axis and wherein the protrusion of the inner member and the groove of the outer member engage to rotationally fix the inner and outer members with respect to each other;

a gear member having gear teeth extending around a perimeter of the gear member from a proximal end of the gear member to a distal end of the gear member;

wherein the at least one protrusion moves with the inner member when the inner member moves relative to the outer member to expand the prosthetic implant.

2. The implant of claim 1, the gear member positioned coaxial to the inner member and outer member and axially fixed to the outer member and freely rotatable with respect to the outer member, wherein the gear member threadedly engages the threaded portion of the inner member.

3. The implant of claim 1, wherein the implant further comprises an opening and at least one slot on an outer surface of the outer member, and wherein the gear member of the expandable implant is configured to engage a gear component of an insertion tool member such that when the gear component is rotated, the gear member of the implant is rotated to either expand or contract the implant.

4. The implant of claim 3, wherein the opening in the outer member extends from the outer surface to the hollow interior portion and at least a portion of the opening is threaded.

5. The implant of claim 4, wherein the opening in the outer member of the implant is configured to engage a distal tip portion that extends beyond the gear component.

6. The implant of claim 5, wherein the at least one slot in the outer member of the implant is configured to engage at least one arm of the insertion tool while the insertion tool is holding the implant.

7. The implant of claim 1, wherein the inner member includes a flattened portion and the outer member includes a flattened portion and wherein the flattened portion of the inner member and the flattened portion of the outer member engage to rotationally fix the inner and outer members with respect to each other.

8. The implant of claim 1, wherein the implant has a longitudinal axis and the gear teeth extend substantially parallel to the longitudinal axis.

9. The implant of claim 1, wherein the implant further comprises a locking ring positioned coaxial to the gear member and configured and dimensioned to be received within the gear member.

10. The implant of claim 1, wherein the inner member, outer member, and gear member are made of polyether ether ketone (PEEK).

11. The implant of claim 1, wherein the implant further comprises a locking member for fixing the inner member with respect to the outer member.

12. The implant of claim 1, wherein the protrusion is a lobe and the groove is correspondingly shaped to the lobe, the lobe and groove cooperate to prevent rotational movement of the inner member with respect to the outer member.

13. The implant of claim 1, wherein the implant further comprises at least one endplate connected to either the inner member or the outer member, and wherein the at least one endplate includes at least one screw hole for receiving a screw.

14. The implant of claim 13, wherein the at least one endplate further comprises a blocking element for blocking the screw from backing out once the screw is seated in the screw hole.

15. The implant of claim 1, wherein the implant further comprises a first endplate and a second endplate.

16. The implant of claim 15, wherein the first endplate is connected to the inner member to engage the first vertebral body and the second endplate is connected to the outer member to engage the second vertebral body.

17. The implant of claim 16, wherein the first and second endplates include at least one bone engaging member extending longitudinally from the endplates.

18. The implant of claim 15, wherein a thickness of the first endplate is different than the thickness of the second endplate.

19. The implant of claim 17, wherein at least one of the first and second endplates is poly-axially rotatable with respect to the inner or outer member.

* * * * *